United States Patent [19]

Lundqwist et al.

[11] 4,018,563
[45] Apr. 19, 1977

[54] ANALYSIS OF LOW ION CONTENTS

[75] Inventors: Nils Rune Lundqwist; Gustav Lennart Dahl, both of Nykoping, Sweden

[73] Assignee: Aktiebolaget Atomenergi, Stockholm, Sweden

[22] Filed: Aug. 15, 1975

[21] Appl. No.: 605,003

[30] Foreign Application Priority Data

Aug. 21, 1974 Sweden ............................ 74106535

[52] U.S. Cl. ............................ 23/230 R; 23/253 R; 204/94; 204/101
[51] Int. Cl.² ................. G01N 31/22; G01N 33/18; C25B 1/24
[58] Field of Search .......... 23/254 E, 255 E, 232 E, 23/230 R, 253 R; 204/94, 101, 1 T, 195 P, 138; 356/213

[56] References Cited
UNITED STATES PATENTS 1,889,779  12/1932  Ebert et al. ........................ 204/138
1,944,738  1/1934   Grebe et al. ................. 23/230 R X
2,752,306  6/1956   Juda et al. ...................... 204/180 R
2,797,149  6/1957   Skeggs ............................ 23/230 R
3,690,835  9/1972   Lovelock ..................... 23/254 E X
3,764,269  10/1973  Oldham et al. .................. 23/254 E
3,920,402  11/1975  Afanasier et al. ................ 23/254 E Primary Examiner—Norman Yudkoff
Assistant Examiner—Barry I. Hollander
Attorney, Agent, or Firm—Burns, Doane, Swecker & Mathis

[57] ABSTRACT

A method of and an apparatus for analysing low halogenide ion contents, the analysis being performed photometrically after an electrodialysis concentration of the halogenide ions, whereby the halogenide ions are also converted into elementary halogen. By said conversion contaminating halogenide does not have any adverse influence on the photometric analysis.

21 Claims, 5 Drawing Figures

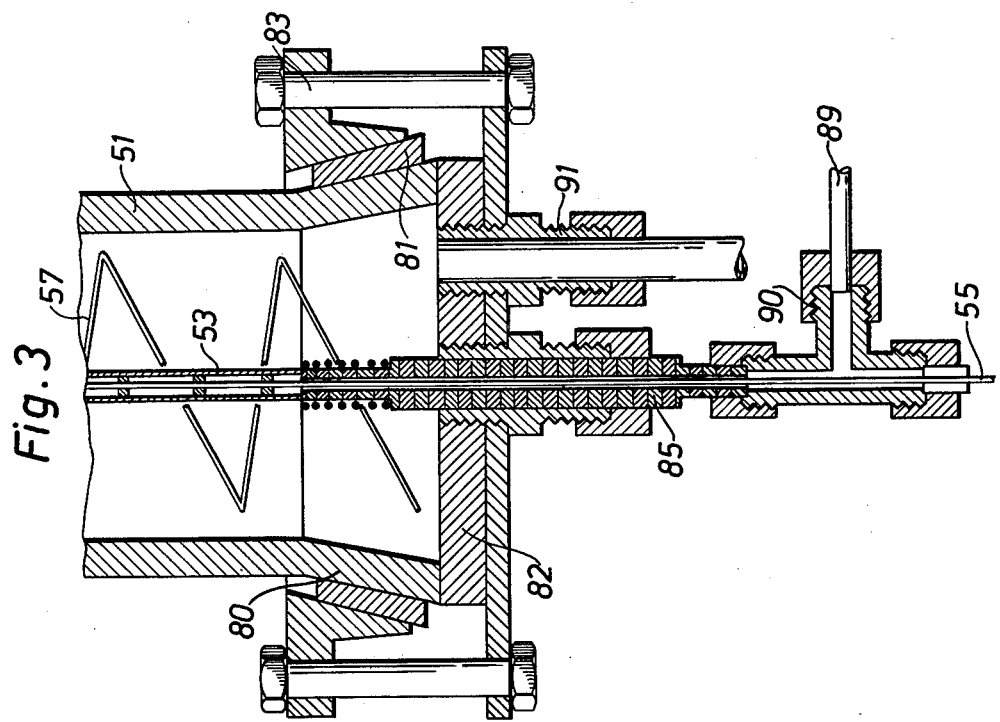
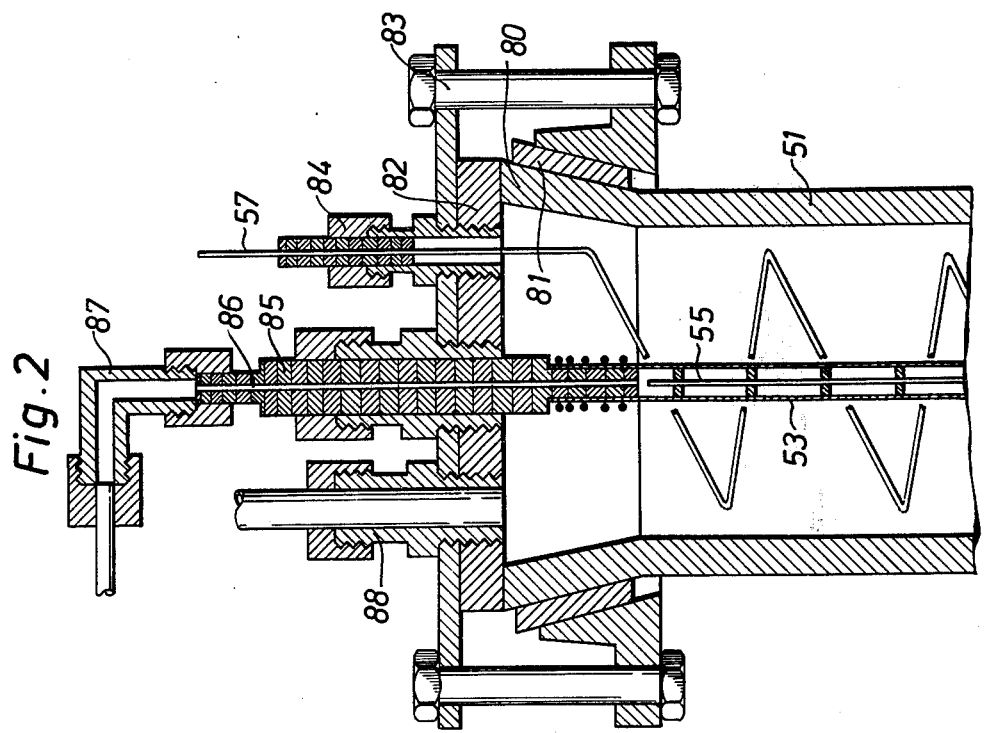

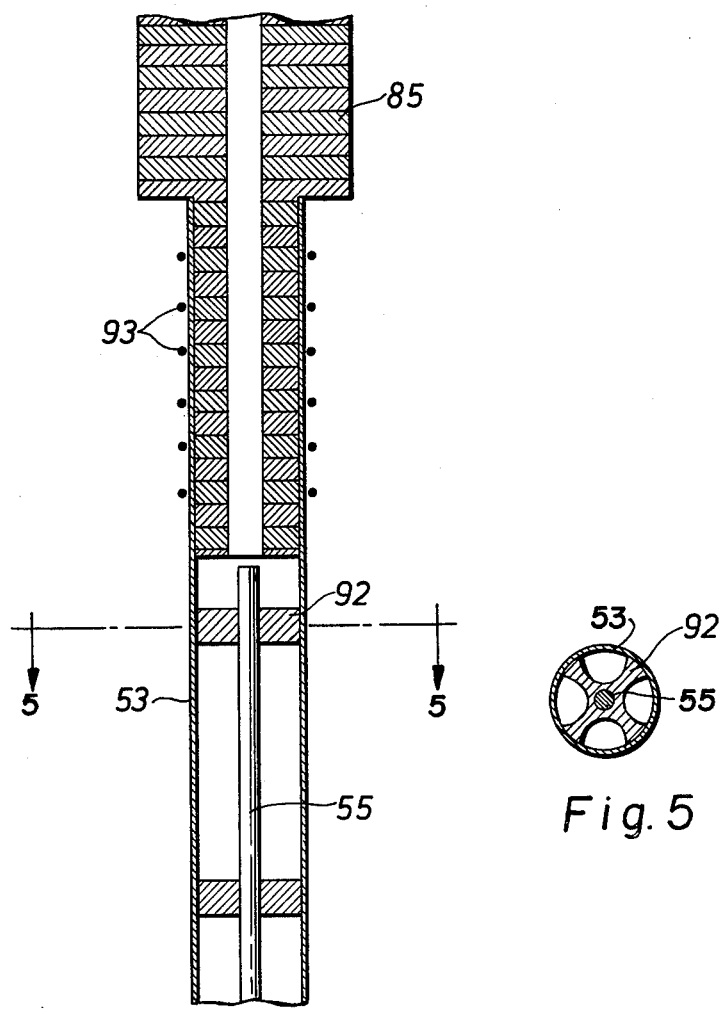

ANALYSIS OF LOW ION CONTENTS

The present invention relates to a method of and an apparatus for analysing low halogenide ion contents in a solution. Although the invention can be generally applied to ionogenic solutions containing halogenide ions selected from the group consisting of chloride, bromide and iodide, it is particularly useful for the analysis, especially the continuous analysis, of low chloride ion contents in high-purity water such as the water used in reactor technology and steam technology, for example condensate.

No satisfactory method of the continuous analysis for example of chloride ions in concentrations of less than around 10 ppb, has thus far been discovered. However, the need for such a method is very great, for example in order to make it possible to detect small continuous leakage from condensors.

The object of the present invention, therefore, is to provide a method of and an apparatus for the preferably continuous analysis of low halogenide ion contents in a solution. This object is achieved by virtue of the fact that the method of and apparatus in accordance with the invention exhibit the features disclosed in the attached claims.

The invention is accordingly based upon initial increase in concentration by a process of electrodialysis, following which the concentrate obtained is analysed photometrically. It is an advantage is this context that analysis of the concentrate is effected not in relation to the original ions but in relation to the elementary form, which can be obtained when using electrodialysis on chloride, bromide or iodide ions. In this fashion, the result is achieved that any occurrence of the ions being analysed, in the reagent added at the photometric analysis of the concentrate, is prevented from affecting the result of analysis.

The invention is applicable to the analysis of chloride, bromide and iodide ions due to the fact that in electrodialysis they can be discharged at an electrode and leave it in elementary form without any risk of becoming attached to the electrode.

The electrical conductivity of the solutions being examined, especially high-purity water, is very often far too low for it to be possible to carry out electrodialysis. Accordingly, the test solution, prior to electrodialysis, has an electrolyte added to it so that the desired conductivity is achieved. The electrolyte will for example be constituted by an acid such as acetic acid or carbonic acid which does not contain the ion which is being analysed. Other advantages and features of the present invention will become apparent from the ensuing description of an embodiment chosen by way of example, taken in conjunction with the attached drawings.

In FIG. 1 there is schematically illustrated the structure of an apparatus in accordance with the invention for the continuous analysis of low chloride ion contents in high-purity water.

FIG. 2 shows more in detail the upper part, in a cross-sectional view, of the electrodialysis apparatus from FIG. 1.

FIG. 3 shows more in detail the lower part, in a cross-sectional view, of the electrodialysis apparatus from FIG. 1.

FIG. 4 shows an enlarged cross-sectional view of the fitting of the dialysis tube from FIG. 2.

FIG. 5 is a cross-section on line 5—5 of FIG. 4 showing one form of a spacer element used for locating the electrode in the dialysis tube.

Figure 1:
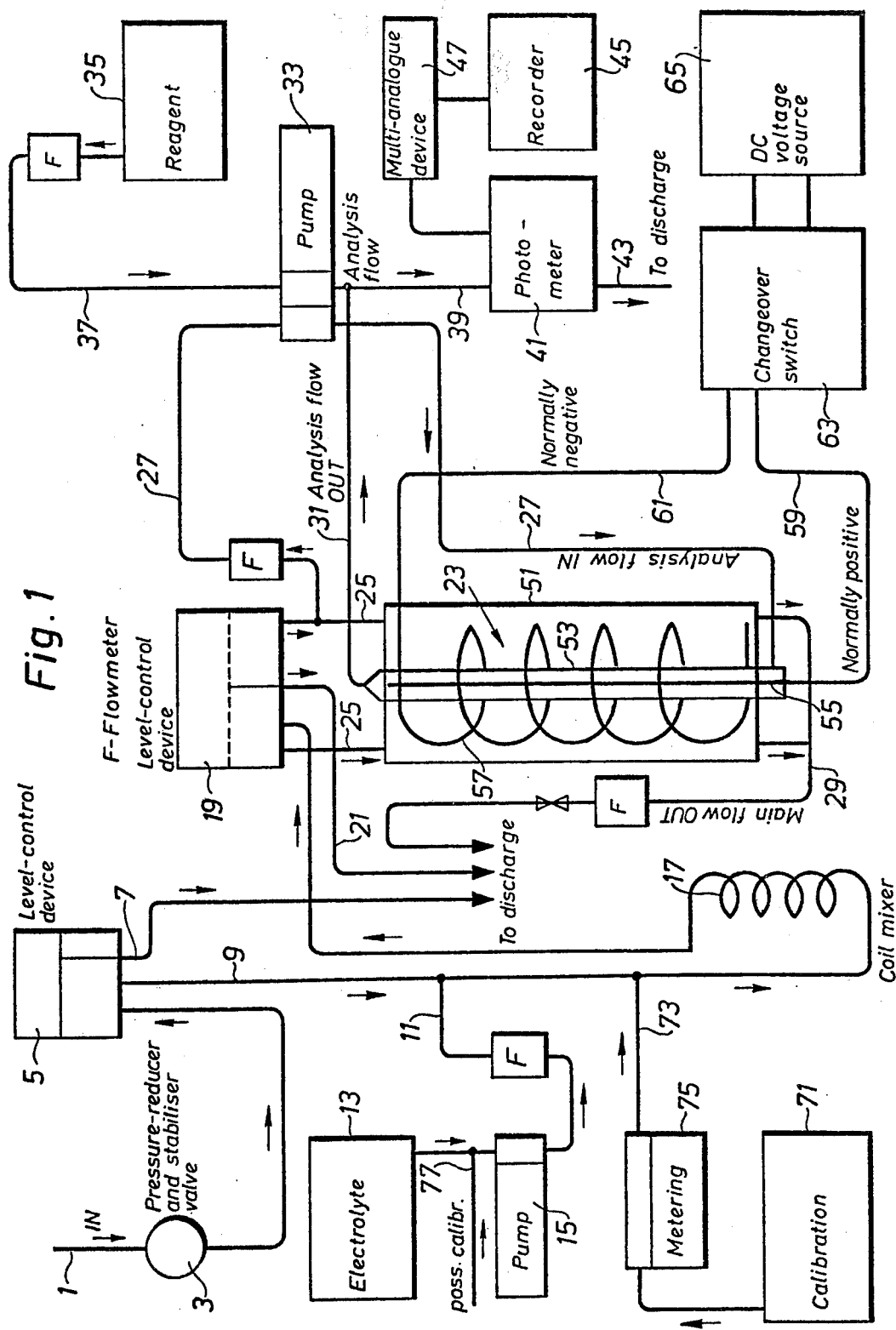

The apparatus shown in FIG. 1 is connected to the solution which is to be analysed, in a continuous fashion, through a line 1 which continuously draws off the test solution. The test solution extracted in this way is cooled if required, to 25° to 30° C and passed through a pressure-reducer and stabiliser valve 3 before flowing into a first level-control device 5 equipped with a weir 7. From the first level-control device 5 a relatively constant flow of test solution is tapped off through a line 9. To the test flow solution passing through the line 9 there is continuously added an electrolyte, this being introduced through a line 11. The electrolyte is metered from a vessel 13 by means of a tube pump 15 arranged in the line 11. The quantity of electrolyte added, will conveniently be selected in such a fashion that the maximum current intensity attainable during electrodialysis well exceeds (for example by 50%) the current intensity which it is calculated electrodialysis should be carried out at.

The test solution from the first level-control device 5 and the electrolyte from the vessel 13 are mixed in a coil mixer 17 which is created quite simply by winding the line 9 in coil fashion, whereafter the test solution with the electrolyte added to it flows into another level-control device 19 located at a lower point than the first one 5 and equipped with a weir 21. From the second level-control device 19, a high-stability test solution flow is tapped off and directed to an electrodialysis apparatus 23 vertically below the device 19. The test solution flow from the level-control device 19 is split into a main flow which is supplied at the top of electrodialysis apparatus 23 through the line 25, and an analysis flow which is supplied at the bottom of electrodialysis apparatus 23 through a line 27. The main flow is extracted at the bottom of the electrodialysis apparatus 23 through a discharge line 29 and the analysis flow is extracted at the top of the electrodialysis apparatus 23, through a line 31.

The analysis flow is regulated by pumping it through the line 27 using a tube pump 33. The same tube pump 33 is used to pump a specific flow of a photometric reagent from a vessel 35 through a line 37. The analysis flow from the line 31 and the reagent flow from the line 37, therefore always have a constant ratio to one another when mixed to form a flow in a line 39 which passes through a flow-metering cell in a photometer 41, to a discharge line 43. An analysis recorder 45 is connected to the photometer 43 through a so-called multi-analogue device 47.

To control the flows through the lines 11, 27, 29 and 37, a flowmeter F is arranged in each of them.

The electrodialysis apparatus 23 comprises a cylindrical, vertical glass tube 51 and an electrodialysis diaphragm arranged centrally therein and taking the form of a cellophane tube 53 the internal diameter of which is small compared with the diameter of the tube 51. Centrally located in the tube 53 there is a first, normally positive electrode 55 in the form of a straight platinum wire. Adjacent the internal wall of the tube 51, there is a second, normally negative electrode 57 in the form of a vertically spiral-wound platinum wire. The electrodes 55 and 57 are connected, via leads 59 and 61, to a changeover switch 63 which is in turn connected to a DC voltage source 65.

During electrodialysis, therefore, the main flow flows downwards through the space between the internal wall of the cuvette 51 and diaphragm tube 53, whilst the analysis flow flows in the opposite direction up through the space inside the diaphragm tube. Consequently, the chloride ions migrate from the main flow through the diaphragm tube into the analysis flow and towards the positive electrode 55. At the electrode, the chloride ions are discharged and converted to elementary chlorine. The chlorine gas which is liberated, is entrained in the analysis flow and dissolves in same. The chlorine reacts in the analysis flow line with the added reagent so that a coloured analysis flow results whose intensity at a specific wavelength is determined in the photometer.

As far as the degree of concentration achieved in the electrodialysis apparatus 23, is concerned, this, within certain limits, is directly proportional both to the current intensity (at constant voltage) and the voltage (at constant current), and to the main flow, as well as inversely proportional to the analysis flow. The degree of concentration can thus easily be varied as required, realistically between 10 and 100 times and will preferably be in the order of magnitude of 20 times.

To calibrate the apparatus in accordance with the drawing, a vessel 71 is provided containing a solution of known chloride ion content, for example 100 ppm NaCl solution, which solution can, through a line 73, be injected in a predetermined quantity into the line 9 prior to the coil mixer 17, using a metering injector arranged in the line 73. At the time of calibration, the connection of the line 1 to the solution which is to be analysed is interrupted, and the line 1 is supplied instead with de-ionised pure water. When a zero line is obtained on the recorder 45, the calibrating solution is injected at a constant rate by means of the injector 75, so that a certain deflection, corresponding to a previously calculated chloride ion content, is obtained on the recorder 45.

Calibration can also be carried out if access to de-ionised pure water is not available. In this case, the apparatus is initially operated in the normal way but the DC voltage across the electrodialysis apparatus 23 is reversed by the changeover switch 63. In this fashion, a zero line is obtained. Thereafter, the changeover switch 63 is returned to its normal position so that an initial deflection is obtained on the recorder 45, this corresponding to the chloride ion content in the solution analysed. At this point, a known flow of calibrated solution is pumped into the line 9 and another deflection is obtained on the recorder 45. The difference between the second and first deflections, represents a known, earlier calculated increase in the chloride ion content and consequently provides the required scale factor.

Another possibility where calibration is concerned, is to pump in turn into the line 9 flow specific of known chloride ion solutions, and to determine the scale factor from the changes in deflection thus obtained. This could for example be done using the tube pump 15, as indicated at 77.

When using the apparatus illustrated in the drawing, deposits generally build up after a time on the electrodes, this leading to a reduction in the degree of concentration achieved. This can be overcome by regularly reversing the direction of flow of the current, using the changeover switch 63. The latter can accordingly be arranged to automatically reverse the direction of current flow for a period of 15 minutes every 4 hours. In this way, the zero line is at the same time defined on the recorder 45.

FIG. 2 shows the upper part of the glass column 51 which is provided with a flare 80 surrounded by an asbestous-graphite gasket 81, a polytetrafluorethylene gasket 82 and a conventional metallic flange coupling 83. The platinum electrode 57 is inserted in the glass column 51 by means of a polypropylene fitting 84 while the other platinum electrode 55 is arranged in the dialysis tube 53 which is in turn connected to a connection piece 85 of polytetrafluoroethylene. The connection piece 85 is provided with a channel 86 for the analysis flow from the electrodialysis apparatus which flow is also passed through a polypropylene fitting 87. The main flow to the electrodialysis apparatus is passed through the polypropylene fitting 88.

In FIG. 3 which shows the lower part of the glass column 51 those elements which are similar to those of FIG. 2 have the same reference numerals as in FIG. 2. In addition to said similar elements FIG. 3 shows the inlet 89 for the analysis flow which is passed in through a polypropylene fitting 90 and the connection piece 85. The main flow from the electrodialysis apparatus is passed through a polypropylene fitting 91.

FIG. 4 shows an enlarged view of the connection piece 85 from FIG. 2 which is connected to the dialysis tube 53 and its electrode 55. The electrode 55 is spaced from the tube 53 by means of polytetrafluoroethylene spacers 92 which are also shown from above in the drawing. The tube 53 is connected to the connection piece 85 by means of a wound wire 93.

The invention will now be further described by means of a specific example as an illustration only.

Example

The method according to the invention was performed while using the equipment below for the analysis of chlorine in high purity water.

| Equipment (The apparatus shown in the drawing was used) | |
| --- | --- |
| Photometer | Turner 330 (G. K. Turner, USA) |
| Multi-analogue device | Optilab 201 (B. Philiph Instrumentation, Sweden) |
| Recorder | T02NI-H 2001 (Tohshin Electron Co. Ltd., Japan) |
| DC voltage source | "Special" (G. Beckman AB, Sweden) |
| Pumps | Masterflex (Cole Parmer Instrument Co., USA) |
| Rotaments | from Fischer & Porter |
| Electrodialysis column | A glass tube having a length of 1 meter and an internal diameter of 65 millimeters and bearing a semipermeable, non-ion selective cellophane tube, the diameter of which was 6 millimeters. As electrodes there were used a straight platinum wire with a length of 1 meter and a diameter of 1 millimeter and a spiral-wound platinum wire with a length of |

| Equipment (The apparatus shown in the drawing was used) |
| --- |
| 5 meters and a diameter of 1 millimeter, respectively. The tube fittings were conventional polypropylene fittings while the gaskets were conventional polytetrafluoroethylene and asbestous-graphite gaskets. |

The rest of the equipment was of a purely conventional type.

As a reagent for the photometric analysis there was used o-tolidine which gives a yellow colour with chlorine, the intensity of which is determined at about 440 nm, in this case at 445 nm. The same reagent is useful when determining bromine or iodine.

The reagent solution used had the following composition: 10 g of o-tolidine were dissolved in 1500 ml of concentrated acetic acid and then diluted to 10 liters using de-ionised and naturally chlorine-free water.

The experiment was run as follows.

From the level-control device 5 a constant flow of test solution of 2150 ml/min was tapped off through line 9. To the test flow solution in line 9 there was continously added 6 ml/min of 0.5% acetic acid. The test flow solution from the level-control device 19 was split into a main flow of 2000 ml/min and an analysis flow of 10 ml/min. After electrodialysis at an output voltage and an output current of respective magnitudes 500 V and 1 A 0.5 ml/min of reagent solution was added to the analysis flow, which was analysed in the photometer provided with a flow cuvette having a length of 15 mm and which was found to have a content of 0.1 ppb of $Cl^-$.

The apparatus described is best suited to measurement of chloride ion contents in a range from 0.1 to 20 ppb (1 ppb = $10^{-6}$ g/liter). However, the range of application of the apparatus should be capable, at the expense of minor modifications, of being extended down to around 0.01 ppb, for example by using a longer flow cuvette in the photometer, for example one having a length of 100 mm, instead of the conventional flow cuvettes which have a length for example of 15 or 50 mm, something which should be entirely viable in the light of the indicated magnitude of the analysis flow.

The importance of the fact that at the electrodialysis the chloride ion is converted into elementary chlorine is illustrated by the following example.

A generally used method of photometrically analysing chloride ions is the mercurythiocyanate method, the analysis being performed on chloride ions.

To 20 ml of test water (concentrated by means of evaporation) the following reagents are added:

| | |
| --- | --- |
| 0.5 ml of 70% $HClO_4$ contaminated by | $1.5 \times 10^{-3}$ mg of $Cl^-$ |
| 0.5 ml of $Hg(SCN)_2$ contaminated by | $2.5 \times 10^{-5}$ mg of $Cl^-$ |
| 0.2 ml of $Fe(ClO_4)_3$ contaminated by | $1.4 \times 10^{-4}$ mg of $Cl^-$ |
| Totally about | $1.6 \times 10^{-3}$ mg of $Cl^-$ |

If the chloride ions of 2000 ml of a test water solution are concentrated to 20 ml of concentrate (to which the reagent is to be added) the total amount of $Cl^-$ in said 20 ml is $2 \times 10^{-3}$ mg if the starting solution (2000 ml) contained 1 ppb of chloride. This is of the same order as the chloride added with the reagent. Even if using at the analysis a comparative solution of all reagents added to an "absolutely pure water" of the same volume as the solution to be tested and subtracting it from the tested sample, it is apparent that one should not analyse samples having lower contents of chloride ions than the sum of the impurities of the reagent solution.

The invention is, of course, not limited to the embodiments described in detail and in fact modifications and changes are possible within the scope of the attached claims. For example, it is possible to use for electrodialysis two or more parallel-connected pieces of electrodialysis apparatuses of the kind referred to, so that the height of the glass tube can be reduced and the size of the apparatus therefore likewise.

What is claimed is:

1. A method of analyzing a solution having low contents of halogenide ions selected from the group consisting of chloride, bromide, and iodide ions to determine the halogenide ion content thereof which comprises (a) extracting a constant test solution flow from the solution to be analyzed; (b) dividing said test solution flow into an analysis flow and a main flow; (c) passing said analysis flow and said main flow over respective sides of an electrodialysis diaphragm; (d) electrolyzing said analysis flow and said main flow to obtain an analysis flow with a halogenide ion concentration higher than that prior to electrodialysis and to convert said halogenide ions in said electrodialyzed analysis flow into elementary halogen, and to obtain a main flow with a halogenide ion concentration lower than that prior to electrodialysis; and then (e) photometrically analyzing the electrodialyzed analysis flow thus obtained to determine its elementary halogen content.

2. A method as claimed in claim 1, wherein an electrolyte is added to the solution to be analyzed prior to electrodialysis in order to increase the electrical conductivity of said solution.

3. A method as claimed in claim 2, wherein the electrolyte is an acid.

4. A method as claimed in claim 3, wherein the acid is acetic acid.

5. A method as claimed in claim 1, wherein the volume ratio between the main flow and the analysis flow is at least 50.

6. A method as claimed in claim 5, wherein said volume ratio is of the order of 200.

7. A method as claimed in claim 1, wherein during electrodialysis the main flow and the analysis flow flow in opposite directions.

8. A method as claimed in claim 1, wherein a photometric reagent is added to the analysis flow after electrodialysis.

9. A method as claimed in claim 8, wherein the reagent is added to the analysis flow after electrodialysis, in such a volume that the volume ratio between the reagent flow and the analysis flow will be constant.

10. A method as claimed in claim 9, wherein the volume ratio between analysis flow and reagent flow is of the order of 20.

11. A method as claimed in claim 1 wherein the analysis is carried out continuously.

12. A method as claimed in claim 11, wherein the direction of the electrodialysis current is reversed at specific time intervals for specific times.

13. A method of continuously analysing low chloride ion contents in high-purity water, which comprises (a) extracting a constant test solution flow from said high-purity water and dividing said test solution flow into an analysis flow and a main flow both of which are passed over respective sides of an electrodialysis diaphragm so as to increase the concentration of chloride ions in the analysis flow as well as to convert the chloride ions into elementary chlorine in the same flow; and then (b) photometrically analysing the concentrated analysis flow from the electrodialysis diaphragm as to its content of elementary chlorine.

14. An apparatus for analyzing a solution of low contents of halogenide ions selected from the group consisting of chloride, bromide, and iodide ions to determine the halogenide ion content thereof which comprises:
   a. means for extracting a constant test solution flow from the solution to be analyzed;
   b. means for splitting said test solution flow into a main flow and an analysis flow;
   c. electrodialysis means having an electrodialysis membrane separating said electrodialysis means into a main flow chamber and an analysis flow chamber;
   d. means for conducting said main flow to said main flow chamber and means for conducting said analysis flow to said analysis flow chamber, said electrodialysis means causing the halogenide ion concentration of the analysis flow to be increased above that of the test solution and to convert the halogenide ions in said analysis flow into elementary halogen, said electrodialysis means also causing the halogenide ion concentration of the main flow to be decreased below that of the test solution; and
   e. means for photometrically analyzing the analysis flow obtained from the electrodialysis means to determine its content of elementary halogen.

15. An apparatus as claimed in claim 14, wherein the analysis flow chamber has its inlet at one end and the main flow chamber has its inlet at the other end of the electrodialysis means.

16. An apparatus as claimed in claim 15, wherein the main and analysis flow chambers are arranged substantially vertically in the electrodialysis apparatus.

17. An apparatus as claimed in claim 16, wherein the analysis flow chamber has its inlet at the bottom of the electrodialysis means.

18. An apparatus as claimed in claim 14, wherein the diaphragm is tubular and arranged in a cylindrical vessel, the space between the vessel walls and the diaphragm forming one chamber and the tubular space inside the diaphragm forming the other chamber, an electrode being arranged around the diaphragm in the said one chamber and an electrode being arranged substantially centrally within the said other chamber.

19. An apparatus as claimed in claim 14, wherein photometric analysis means comprises a photometer and means for adding reagent to the analysis flow coming from the electrodialysis means.

20. An apparatus as claimed in claim 19, wherein said means for adding reagent comprises a pump which simultaneously pumps the analysis flow through the electrodialysis means, whereby the volume ratio between the reagent flow and the analysis flow can be kept constant.

21. An apparatus as claimed in claim 14, wherein means are provided for adding an electrolyte to the test solution prior to electrodialysis.

* * * * *